United States Patent [19]
Rosinko

[11] Patent Number: 5,565,977
[45] Date of Patent: Oct. 15, 1996

[54] SYSTEMS AND METHODS FOR IDENTIFYING AND CONTROLLING INTERFACES BETWEEN BLOOD COMPONENTS

[75] Inventor: Michael J. Rosinko, Brea, Calif.

[73] Assignee: Baxter International Inc., Deerfield, Ill.

[21] Appl. No.: 482,363

[22] Filed: Jun. 7, 1995

[51] Int. Cl.$^6$ ................................................ G01N 33/48
[52] U.S. Cl. ........................ 356/39; 250/573; 250/577; 73/61.69
[58] Field of Search ........................ 356/39, 432, 433, 356/434, 435, 436; 73/61.69; 250/573, 577; 364/413.07, 413.09

[56] References Cited

U.S. PATENT DOCUMENTS

| 4,194,391 | 3/1980 | Rosenberger | 73/61.69 |
| 4,450,722 | 5/1984 | Keyes, IV et al. | 250/577 |
| 5,463,228 | 10/1995 | Krause | 250/577 |

Primary Examiner—Frank Gonzalez
Assistant Examiner—Robert Kim
Attorney, Agent, or Firm—Daniel D. Ryan; Bradford R. L. Price; Joseph B. Barrett

[57] ABSTRACT

Systems and methods locate at least three spaced apart sensing units in association with volume of blood comprising a first blood component region, a second blood component region, and an interface region between the first and second blood component regions. The systems and methods locate at least one of the sensing units so that its optical field lies above the interface region and at least one of the sensing units so that its optical field lies below the interface region. Each sensing unit senses the attenuation of energy emitted into blood in its optical field and generates a signal relating to the attenuation. The systems and methods convert the signals to a signal vector of signal values having a shape approximated by a function. The systems and methods normalize the signal vector, and also create a vector of convolution signal values by multiplying the normalized signal vector by the function. The systems and methods identify the sensing unit associated with the highest convolution signal value. It is this sensing unit that lies closest to the interface. The systems and methods can limit the signal values of the signal vector according to prescribed criteria that eliminate the effect of noise.

24 Claims, 5 Drawing Sheets

SYSTEMS AND METHODS FOR IDENTIFYING AND CONTROLLING INTERFACES BETWEEN BLOOD COMPONENTS

FIELD OF THE INVENTION

The invention generally relates to blood collection and processing systems and methods. In a more particular sense, the invention relates to systems and methods for locating interfaces between different blood components.

BACKGROUND OF THE INVENTION

Most of the whole blood collected from donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

During centrifugal blood processing, an interface develops between the red blood cell and plasma components. Leukocytes occupy this interface, which is also referred to as the buffy coat.

In collecting whole blood components for transfusion, it is desirable to minimize the presence of impurities or other materials that may cause undesired side effects in the recipient. For example, because of possible febrile reactions, it is generally considered desirable to transfuse red blood cells and plasma substantially free of leukocytes, particularly for recipients who undergo frequent transfusions.

It is therefore important during blood processing to be able to accurately identify the leukocyte-rich interface between red blood cell and plasma components, so that processing can be controlled to isolate the interface from the other components. This need exists not only for automated blood collection procedures, but also for manual blood collection procedures.

Conventional systems and methods often employ optical signal processing to identify and control the interface. Such systems often have limited tolerance to "noise", which leads to false readings. Such noise can arise due to variations in the performance of the optical elements, especially when multiple optical elements are used in tandem, since optical elements are known to have a high degree of variability in gain, focus, and directivity. Mechanical vibration is another source of noise.

Blood components are "sticky" and can smear along the sides of a separation chamber or bag. The smearing is yet another category of noise, as it leads to false readings and the incorrect identification of the interface.

SUMMARY OF THE INVENTION

The invention provides systems and methods that consistently provide accurate monitoring of a volume of blood, despite the presence of noise of all types.

The systems and methods locate at least three spaced apart sensing units in association with volume of blood comprising a first blood component region, a second blood component region, and an interface region between the first and second blood component regions. The systems and methods locate at least one of the sensing units so that its optical field lies above the interface region and at least one of the sensing units so that its optical field lies below the interface region. Each sensing unit senses the attenuation of energy emitted into blood in its optical field and generates a signal relating to the attenuation.

The systems and methods convert the signals to a signal vector of signal values having a shape approximated by a function. The systems and methods normalize the signal vector, and also create a vector of convolution signal values by multiplying the normalized signal vector by the function. The systems and methods identify the sensing unit associated with the highest convolution signal value. It is this sensing unit that lies closest to the interface.

In a preferred embodiment, the systems and methods limit the signal values of the signal vector according to prescribed criteria that eliminate the effect of noise.

In a preferred embodiment, the systems and methods generate an output relating to the identity of the sensing element associated with the highest convolution signal value. This output can be used, for example, to limit travel of the interface region within a container while the first or second blood component regions are conveyed from the container.

In a preferred embodiment, the function is a sigmoidal function, and the normalized signal vector has a shape symmetric about −1 and 1.

Other features and advantages of the invention will become apparent upon review of the following description, drawings, and appended claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
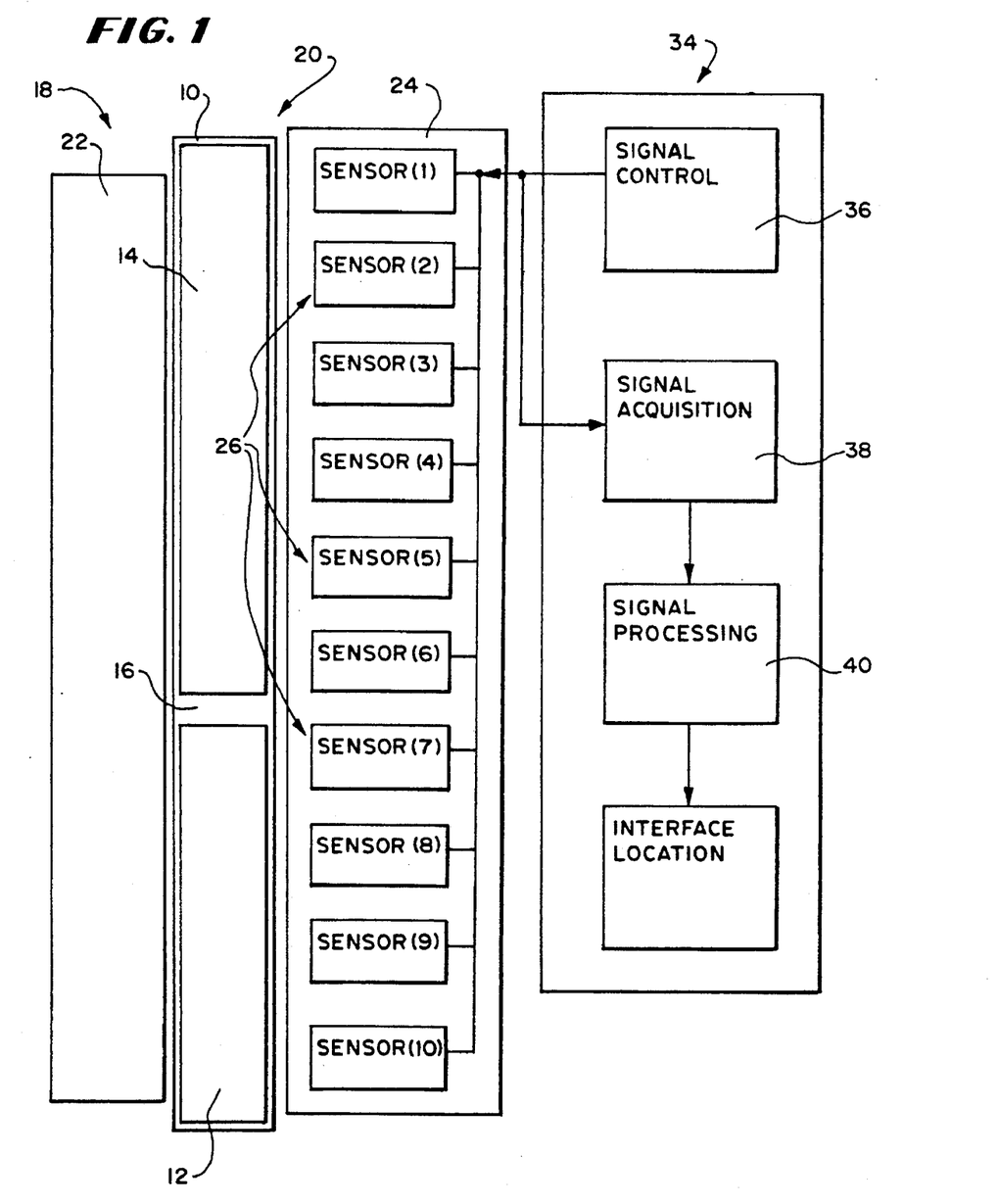
FIG. 1 is a somewhat schematic view of a blood collection system that includes an signal processor that identifies the location of the interface between blood components according to the features of the invention.

FIG. 1 shows a container 10 made of flexible, transparent plastic material containing a unit of whole blood. The whole blood has been centrifugally separated into component parts within the container 10 by conventional techniques.

As FIG. 1 shows, the heavier red blood cell component 12 of whole blood collects where the greatest g-field forces are generated during centrifugation, which FIG. 1 shows to be the bottom of the container 10. The lighter plasma component 14 of whole blood collects where least g-field forces are generated, which FIG. 1 shows to be the top region of the container 10.

During centrifugal separation, an intermediate layer 16 of leukocytes (commonly called the "interface" or "buffy coat") forms between the red blood cell component and the plasma component. If the plasma component is platelet-poor plasma (PPP), the interface 16 also includes a substantial amount of platelets. If the plasma component is platelet-rich plasma (PRP), substantially fewer of platelets remain in the interface 16. Whether the separation process provides PRP or PPP plasma component depends upon the rotational speed and time of processing. Slower rotational speeds over a given time period (called a "soft" spin) produce PRP. Higher rotational speeds over the same time period (called a "hard" spin) yield fewer platelets in the plasma, and produce PPP.

FIG. 1 shows the container 10 held in a system 18 which optically identifies the location of the interface 16. The system includes a holding station 20 comprising a back plate 22 and a front plate 24, which sandwich the container 10 and its contents between them.

The front plate 24 includes an array of sensors units 26. The number of sensor units 26 can vary according to the size of the container and the sensitivity required. Ten sensor units 26 are shown for the purpose of illustration. The sensor units 26 are designated Sensor [1] to Sensor [N], where Sensor [1] is the topmost sensor unit and Sensor N is the bottommost sensor unit. The spacing between sensor units 26 is selected such that Sensor [1] will always be above the interface 16 and Sensor [N] will always be below the interface 16.

In the illustrated embodiment, each sensor unit 26 (see FIG. 2) comprises a light emitting diode (LED) 28 and a photo transistor 30 vertically stacked one on top of the other and both directed toward the container 10. As FIG. 2 best shows, the LED 28 emits energy through the transparent material of the container 10 and the contents which lie in its optical field 60. The surface of the back plate 22 is made of a material that reflects the energy the LED 28 emits. The reflected energy passes back through the container 10 and its contents and is received by the photo transistor 30 within its optical field 62.

In a preferred embodiment (see FIG. 2), a label 32 is applied to the wall of the container 10 that sits against the back plate 22. The label 32 includes an interior surface that reflects the energy emitted by the LED 28 back to the photo transistor 30.

Figure 2:
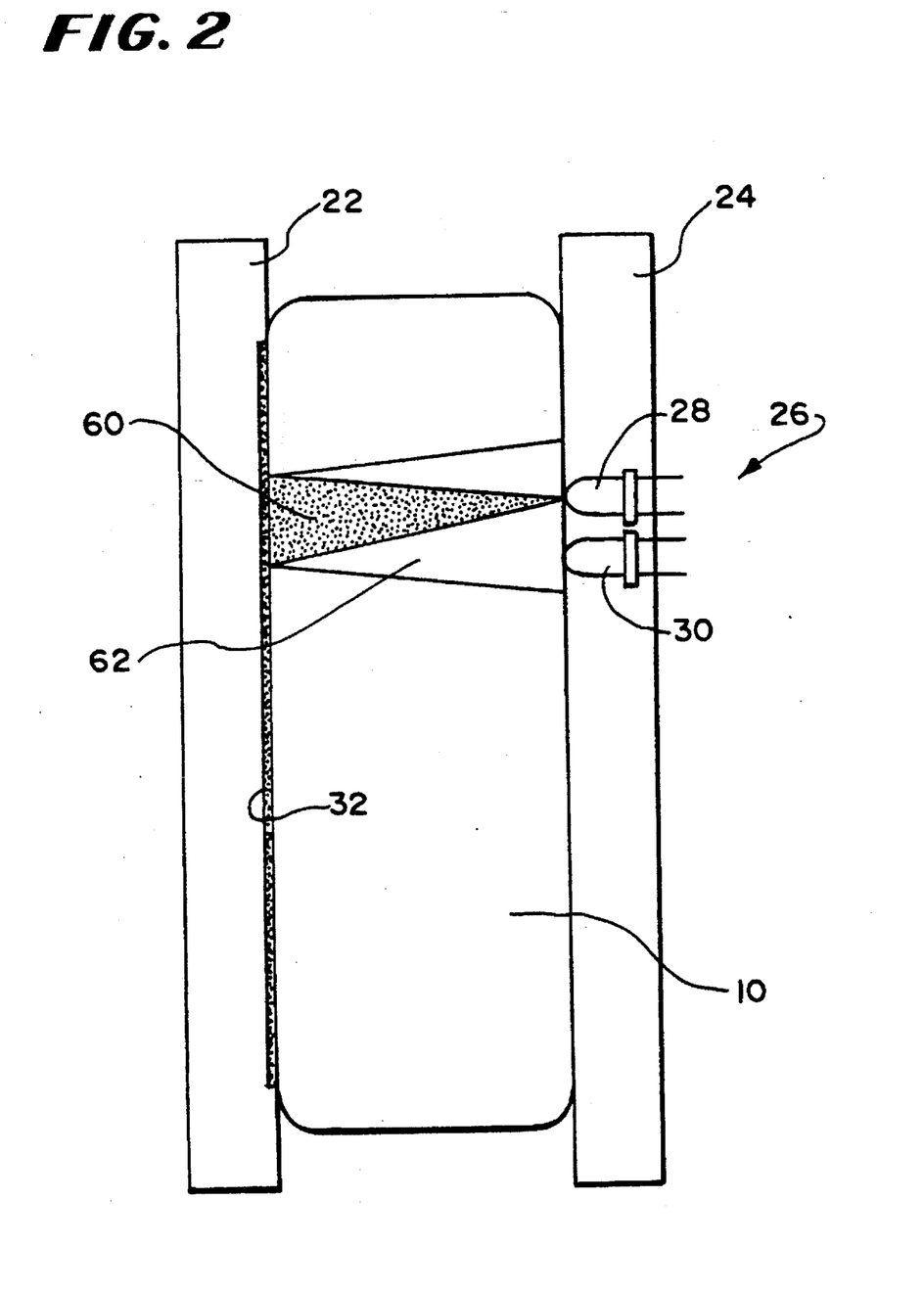
FIG. 2 is an enlarged view of a portion of the system, showing one of the multiple sensors that generates signals for processing by the signal processor.

In an alternative embodiment, the LED 28 and photo transistor 30 of each sensor unit can be arranged in facing, oppositely spaced relationship, one on the front plate 24 and the other on the back plate 22.

The photo transistor 30 generates an analog signal, the magnitude of which is dependent upon the level of attenuation that the energy emitted by the LED 28 experiences upon passing through the contents lying in its optical field 60. The emitted energy is selected so that the red blood cell component 12 provides a high level of attenuation, while the plasma component 14 provides a significantly lower level of attenuation. The interface 16 lies at the threshold between these two different attenuation levels.

The system 18 includes a signal processor 34 (see FIG. 1), which analyses the attenuation of the signals generated by the sensor units 26 for the purpose of locating the interface 16. The signal processor 34 includes a sensor controller 36 coupled to each LED 28. The controller 36 turns the LEDs 28 on sequentially from top to bottom, or vice versa. The signal processor 34 includes a data acquisition element 38 coupled to the photo transistors 30. The data acquisition element 38 periodically samples the analog signals coming sequentially from each photo transistor 30. The data acquisition element 38 converts each analog signal to digital form.

The signal processor 34 further includes a processing element 40 that receives the digital signals from the data acquisition element 38. According to the invention, the processing element 40 converts the digital signals to a 1×N column vector, designated Signal [*]. The shape of the Signal[*] vector gives a large relative value for the sensor units 26 above the interface 16 and a small relative value below the interface 16. The shape of the Signal[*] vector is approximated by the following sigmoidal function:

$$S(y) = \frac{K}{1 + e^{-\alpha(y-y_0)}} + \epsilon \quad (1)$$

where

K is the maximum signal level through the plasma component;

$y_0$ is the Sensor[$y_0$] position where the signal equals ½K, which is the location of the transition where the interface 16 resides;

$\alpha$ is a random variable that determines the steepness of the transition of the function from K to O. The parameter is set by the operator. In the preferred embodiment, $\alpha \approx 3$; and $\epsilon$ is a parameter for noise, which accounts for the variability of optical components, the non-homogeneous nature of blood components, and variations in the reflective system including the reflective nature of the back plate 22 or label 32 and any non uniform or curved surface in the back plate 22 or front plate 24.

In estimating the location of the transition (i.e., the interface), the processing element 40 (see FIG. 3) first normalizes the Signal[*] vector to be symmetrical between −1 and 1. The normalization function SigNorm[i] is expressed as follows:

$$\forall\, i,\, i \in \{1, \ldots, N\}$$

$$SigNorm[i] = 2 \frac{Signal[i] - \min(Signal[*])}{\max(Signal[*]) - \min(Signal[*])} - 1 \quad (2)$$

where:

signal[i] is the digital signal of Sensor[i];

min(Signal[*]) is the smallest digital signal received from all the sensor units; and max(Signal[*]) is the largest digital signal received from all the sensor units.

Figure 3:
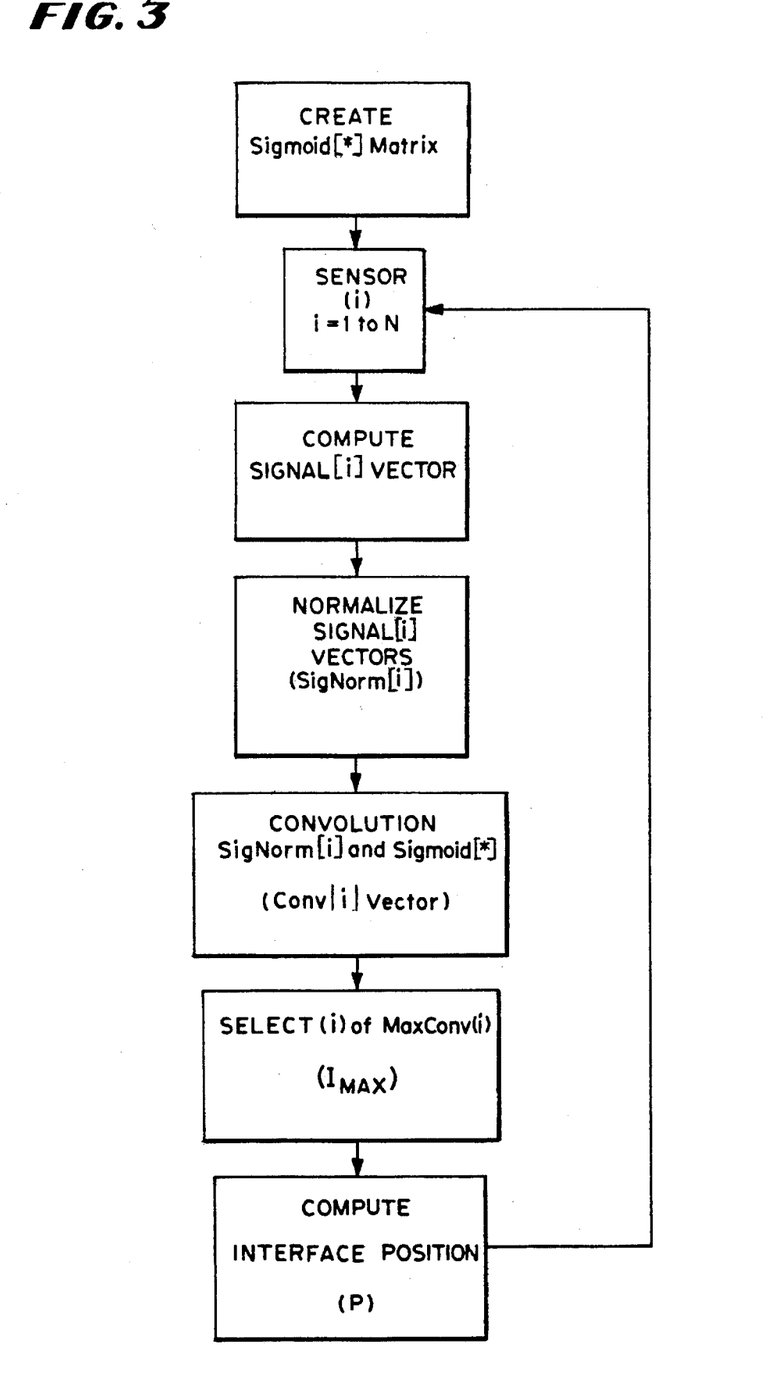
FIG. 3 is a schematic flow chart showing the operation of the signal processor.

Next, the processing element 40 creates an N×N matrix, Sigmoid[*], as a series of row vectors. Each row vector is constructed as the value of the sigmoidal function (from Equation 1) with K=1, $\epsilon$=0, $y_0$=0, and y ranging from −N+1 to 0 for the first row and from 0 to N for the last row, expressed as follows:

$$Sigmoid[*] = \begin{bmatrix} S(-N+1) & S(-N+2) & \ldots & S(0) \\ \cdot & \cdot & & \cdot \\ \cdot & \cdot & & \cdot \\ \cdot & \cdot & & \cdot \\ S(-1) & S(0) & \ldots & S(N-2) \\ S(0) & S(1) & \ldots & S(N-1) \end{bmatrix} \quad (3)$$

The sigmoid[*] matrix needs to be calculated only once, given the number of sensor units 26 and assuming a value for $\alpha$.

Next, the processing element 40 generates a column vector, Conv[*], by performing a matrix multiplication of the Sigmoid[*] matrix (from Equation 3) and the SigNorm[*] column vector (from Equation 2), expressed as follows:

$$Conv[*] = Sigmoid[*] \times SigNorm[*] \quad (4)$$

where:

the operator "x" indicates matrix multiplication and not the cross product operator.

Equation 4 is equivalent to performing a convolution of the SigNorm[*] vector (Equation 2) with the sigmoidal function of Equation 1.

The processing element 40 selects the index of the maximum value of the Conv[*] vector ($I_{MAX}$) as the index closest to the level of the interface 16.

The position of the interface (P) can be estimated to finer than integer resolution as follows:

$$P = N + 1 - I_{MAX} - \frac{Conv[I_{MAX}+1] - Conv[I_{MAX}-1]}{2m} \quad (5)$$

where:

m is the larger of the difference between $Conv[I_{MAX}]-Conv[I_{MAX}+1]$ and $Conv[I_{MAX}]-Conv[I_{MAX}-1]$.

The above methodology provides an accurate estimate of the optical signal marking the transition from the plasma component to the red blood cell component under a wide range of operating conditions. The methodology also provides a high degree of tolerance to the differences between optical signal intensity due to variations in LED intensities, variations in photo transistor sensitivities, and changes in distance between the back plate 22 and the sensor units 26 in the front plate 24.

EXAMPLE

Ten sensor units arranged as shown in FIG. 1 acquire signals as set forth in the following Table 1:

TABLE 1

DIGITAL SIGNALS BY SENSOR[i]

| Sensor [i] | Digital Signal |
| --- | --- |
| Sensor (1) | 200 |
| Sensor (2) | 200 |
| Sensor (3) | 200 |
| Sensor (4) | 200 |
| Sensor (5) | 200 |
| Sensor (6) | 200 |
| Sensor (7) | 200 |
| sensor (8) | 100 |
| Sensor (9) | 0 |
| Sensor (10) | 0 |

The normalized signal vector SigNorm[i] computed according to Equation 2 (with α=3) is set forth in the following Table 2:

TABLE 2

SigNorm[i] VECTOR

| Sensor [i] | SigNorm[i] |
| --- | --- |
| Sensor (1) | 1 |
| Sensor (2) | 1 |
| Sensor (3) | 1 |
| Sensor (4) | 1 |
| Sensor (5) | 1 |

TABLE 2-continued

SigNorm[i] VECTOR

| Sensor [i] | SigNorm[i] |
| --- | --- |
| Sensor (6) | 1 |
| Sensor (7) | 1 |
| Sensor (8) | 0 |
| Sensor (9) | −1 |
| Sensor (10) | −1 |

The 10×10 matrix Sigmoid[*] computed according to Equation 3 (with α=3) is set forth the following Table 3:

TABLE 3

SIGMOID[*] MATRIX

| | | | | | | | | | |
| --- | --- | --- | --- | --- | --- | --- | --- | --- | --- |
| 1.00 | 1.00 | 1.00 | 1.00 | 1.00 | 1.00 | 1.00 | 1.00 | 0.95 | 0.50 |
| 1.00 | 1.00 | 1.00 | 1.00 | 1.00 | 1.00 | 1.00 | 0.95 | 0.50 | 0.05 |
| 1.00 | 1.00 | 1.00 | 1.00 | 1.00 | 1.00 | 0.95 | 0.50 | 0.05 | 0.00 |
| 1.00 | 1.00 | 1.00 | 1.00 | 1.00 | 0.95 | 0.50 | 0.05 | 0.00 | 0.00 |
| 1.00 | 1.00 | 1.00 | 1.00 | 0.95 | 0.50 | 0.05 | 0.00 | 0.00 | 0.00 |
| 1.00 | 1.00 | 1.00 | 0.95 | 0.50 | 0.05 | 0.00 | 0.00 | 0.00 | 0.00 |
| 1.00 | 1.00 | 0.95 | 0.50 | 0.05 | 0.00 | 0.00 | 0.00 | 0.00 | 0.00 |
| 1.00 | 0.95 | 0.50 | 0.05 | 0.00 | 0.00 | 0.00 | 0.00 | 0.00 | 0.00 |
| 0.95 | 0.50 | 0.05 | 0.00 | 0.00 | 0.00 | 0.00 | 0.00 | 0.00 | 0.00 |
| 0.50 | 0.05 | 0.00 | 0.00 | 0.00 | 0.00 | 0.00 | 0.00 | 0.00 | 0.00 |

The column vector Conv[*] computed according to Equation 4 is set forth in the following Table 4:

TABLE 4

CONV[*] COLUMN VECTOR

| Sensor [i] | Conv[i] |
| --- | --- |
| Sensor (1) | 5.5473 |
| Sensor (2) | 6.44997 |
| Sensor (3) | 6.90007 |
| Sensor (4) | 6.44738 |
| Sensor (5) | 5.49727 |
| Sensor (6) | 4.49986 |
| Sensor (7) | 3.5 |
| Sensor (8) | 2.50013 |
| Sensor (9) | 1.5026 |
| Sensor (10) | 0.55003 |

Based upon Table 4, $I_{MAX}=3$.

Based upon Table 4:
  $Conv(I_{MAX}-1)=6.44997$
  $Conv(I_{MAX})=6.90007$
  $Conv(I_{MAX}+1)=6.44738$
  $m=0.4527$ Based upon these values, P is calculated according to Equation 5 as being 8.00.

Figure 4:
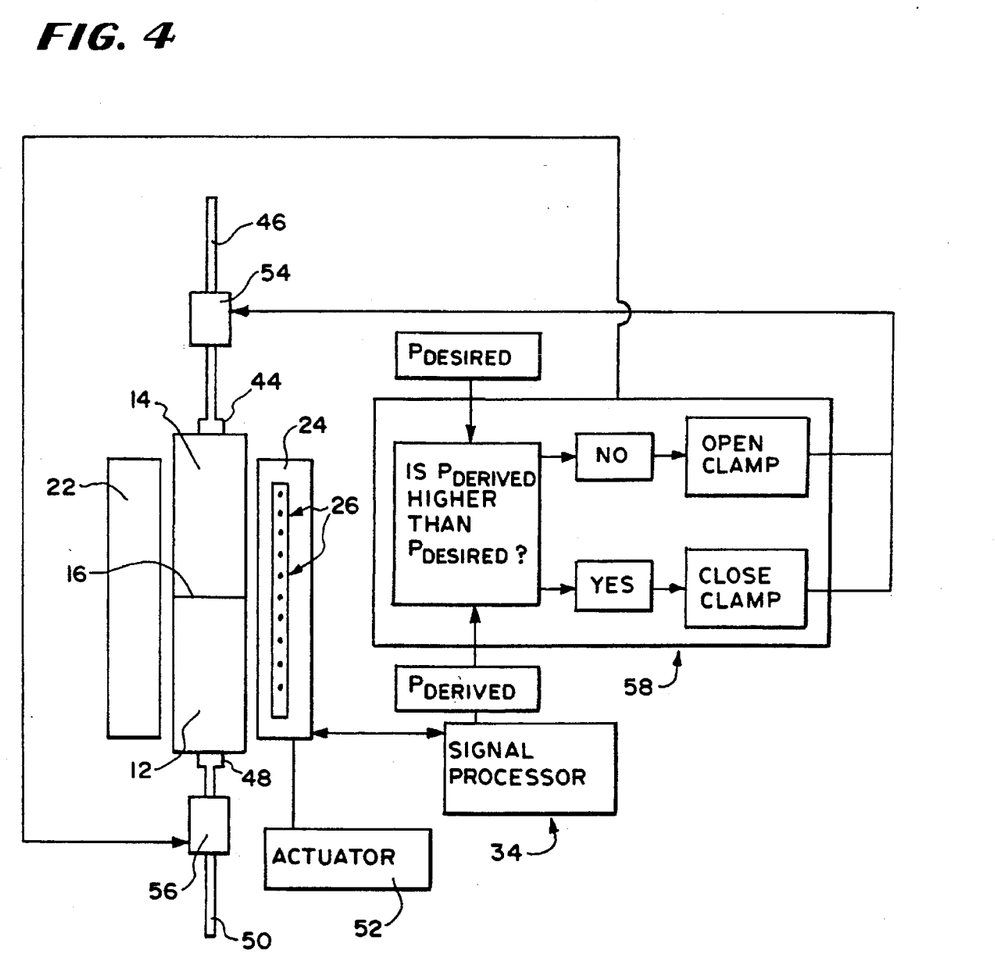
FIG. 4 is a somewhat schematic view of a blood processing system that incorporates the signal processor shown in FIG. 1 for controlling the collection of blood components.

FIG. 4 shows a blood collection apparatus 42 for the container 10, which uses the system 18 as just described for transferring plasma component 14 and red blood cell component 12 from the container 10. The apparatus 42 includes the front and back plates 22 and 24 to hold the container 10, as already described. In FIG. 4, the container 10 includes a top port 44 with associated flexible tubing 46 and a bottom port 48 with its own associated flexible tubing 40. The apparatus 42 also includes the array of sensor units 26 (again numbering 10 for the purpose of illustration) coupled in association with the signal processor 34, as already described.

The apparatus 42 further includes an actuator 52 for moving one of the plates 22/24 with respect to the other plate. In FIG. 4, the actuator 52 moves the front plate 24 toward the the back plate 22. This movement squeezes the container 10 between the plates 22/24. The compression expresses the plasma component 14 from the top port 44 into the associated tubing 46, for example, for collection in a transfer bag (not shown). The red blood cell component 12 is also expressed by the same action from the bottom port 48 into the associated tubing 50, for example, into another transfer bag (not shown).

The apparatus 42 includes electrically actuated solenoid clamps 54 and 56, which are operatively associated, respectively, with the top and bottom tubing 46 and 50. The signal processor 34 monitors the position of the interface 16 in the container 10 as the plasma and red blood cell components 12 and 14 are expressed from the container 10.

The apparatus 42 further includes a clamp controller 58. The clamp controller 58 coordinates operation of the clamps 54 and 56 in response to the signal processor 34, to keep the interface 16 sandwiched between the plasma component 14 and the red blood cell component 12 within the container 10, while the plasma and red blood cell components 12/14 are expressed from the container. This technique retains the interface 16 in the container 10 and, with it, most of the leukocytes for subsequent harvesting or disposal. This technique provides from about 0.75 to about 1.00 log reduction in the number of leukocytes in the plasma component and the red blood cell component, when compared to the leukocytes contained in the whole blood.

In the illustrated embodiment, the clamp controller 58 opens both clamps 54/56 as the actuator 52 moves the front plate 24 to begin the expression of plasma and red blood cell components 12/14 from the container 10. The signal processor 34 continuously derives and outputs either $I_{MAX}$ or P in the manner already described, thereby identifying the position of the interface 16 in the container 10. The clamp controller 58 compares this output to a desired location for the interface 16. The desired location is set by the operator, typically near the middle sensor unit.

If the interface position derived by the signal processor 40 is higher than the desired location, the clamp controller 58 commands the top clamp 54 to close, blocking further exit of the plasma component 14. The interface 16 will fall as the red blood cell component 12 continues to be expressed from the container 10 through the still open tubing 46.

The clamp controller 58 continues to compare the interface position derived by the signal processor 40 with the desired location. When the derived interface position is lower than the desired position, the clamp controller 58 commands the top clamp 54 to open, and plasma component 14 again exits the container 10 along with the red blood cell component 12. The plasma component 14 is less viscous than the red blood cell component 12, and thus flows more quickly from the container 10, so the interface 16 may again rise. Nevertheless, working together, the signal processor 40 and clamp controller 58 maintain the interface 16 at the desired location within the container 10.

If it is desired to control the expression of two fluids with similar viscosities, the clamps 54/56 can be controlled as follows: clamp 54 is controlled as previously described, and clamp 56 is controlled to be in the opposite state as clamp 54.

The methodology uses information from all sensor units, not just the sensor unit where the interface 16 is sought to be stabilized. Thus, a smooth signal is generated should the interface 16 move from sensor unit to sensor unit above and below the desired position.

As plasma and red blood cell components 12/14 are expressed from the container, the interface 16 will move within a prescribed range within the container 10. During this movement, red blood cells and/or leukocytes in the interface 16 can "stick" to the interior wall of the container. This, in turn, can falsely attenuate the optical signals when the interface 16 drops lower than the region where the cells are stuck to the container wall.

In a preferred embodiment (see FIG. 5), the signal processor 40 takes into account the possible presence of cells stuck to the interior wall of the container. In this embodiment, the signal processor 40 truncates the values of the largest digital signals by a prescribed amount before deriving the normalized function SigNorm[i].

Figure 5:
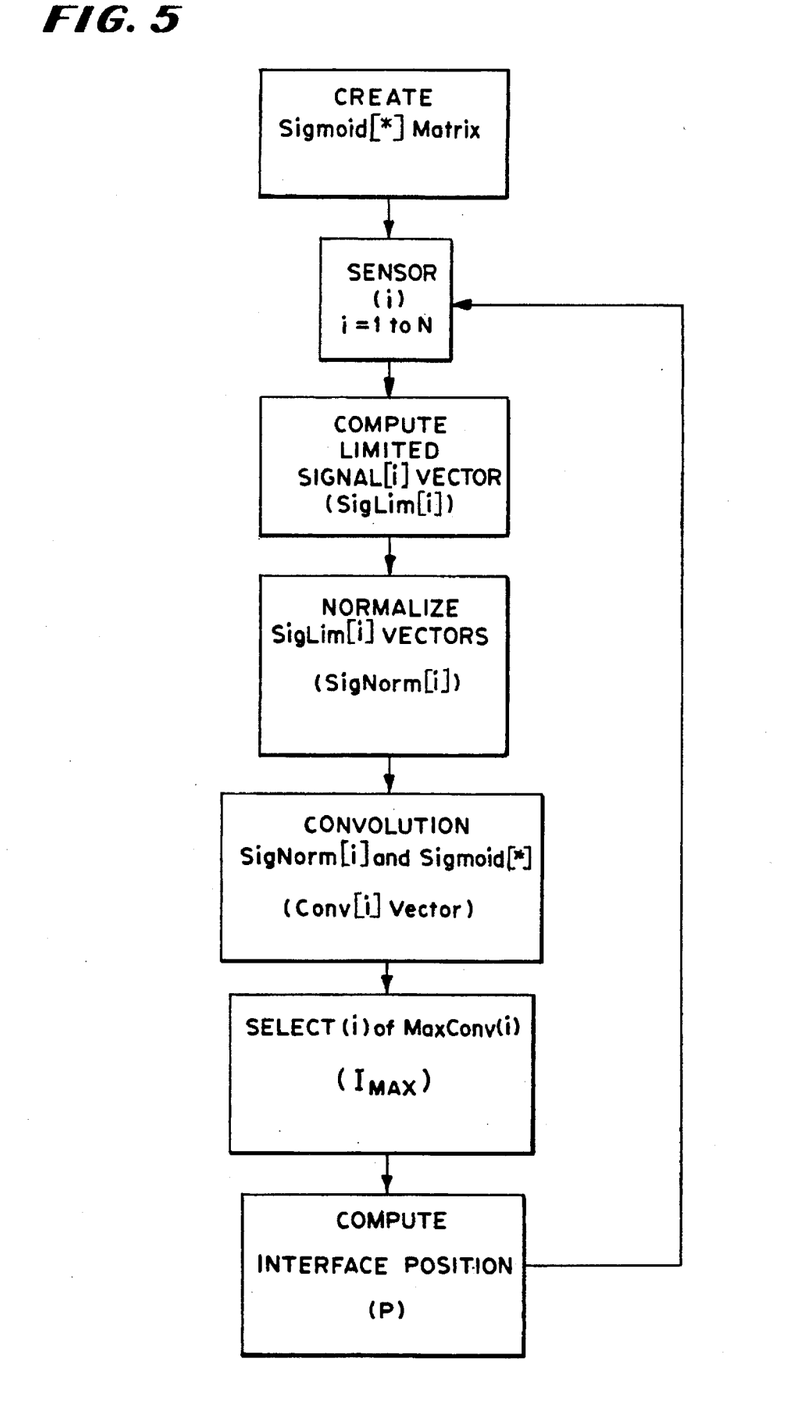
FIG. 5 is a schematic flow chart showing the operation of a preferred embodiment of the signal processor, which takes into account noise caused by smearing of sticky blood components.

More particularly, in this embodiment, the signal processor 40 first limits the vector Signal[*], creating a limited signal vector SigLim[*], as follows:

$$\forall i, i \in \{1, \ldots, N\}$$

$$SigLim[i] = min[Signal[i], T \times max(Signal[*])] \quad (6)$$

where:

max(Signal[*]) is the largest digital signal received from all the sensor units;

T is a truncation factor, where 0<T<1, and is selected based upon the operating parameters of the particular system based upon the degree of false attenuation experienced. In a system like that shown in FIG. 4, where the degree of attenuation by sticky red blood cells and/or leukocytes can be as much as about 0.85 (85%), T is selected to be about 15% (0.15); and the expression min[x,y] selects the value of x or y that has the least numerical value.

In this embodiment, the signal processor 40 generates the vector SigNorm[i] based upon SigLim[*] as follows:

$$\forall i, i < N$$

$$SigNorm[i] = 2 \frac{SigLim[i] - min(SigLim[*])}{max(SigLim[*]) - min(SigLim[*])} - 1 \quad (7)$$

where:

SigLim[i] is the limited digital signal of Sensor[i] according to Equation 6;

min(SigLim[*]) is the smallest limited digital signal according to Equation 6; and max(SigLim[*]) is the largest limited digital signal according to Equation 6.

In all other respects, the signal processor 40 manipulates the optical signal information to derive $I_{MAX}$ or P as previously described.

Various features of the invention are set forth in the following claims:

I claim:

1. A system for monitoring a volume of blood comprising a first blood component region, a second blood component region, and an interface region between the first and second blood component regions comprising at least three spaced apart sensing units that each senses the attenuation of energy emitted into the blood and generates a signal relating to the attenuation, at least one of the sensing units being located with respect to the blood volume above the interface region and at least one of the sensing units being located with respect to the blood volume below the interface region, and a processing element coupled to the sensing units that locates the sensing unit closest to the interface region by steps of converting the signals to a signal vector of signal values having a shape approximated by a function, normalizing the signal vector, creating a vector of convolution signal values by multiplying the normalized signal vector by the function, and identifying the sensing unit associated with the highest convolution signal value.

2. A system according to claim 1 and wherein the processing element performs the step of limiting the signal values of the signal vector according to prescribed criteria.

3. A system according to claim 1 and wherein the processing element includes an output for outputting the identity of the sensing unit associated with the highest convolution signal value.

4. A system according to claim 1 wherein the function is a sigmoidal function.

5. A system according to claim 1 wherein the normalized signal vector has a symmetric shape.

6. A system according to claim 1 wherein the normalized signal vector is normalized between −1 and 1.

7. A system for monitoring the contents of a container holding blood comprising a first blood component region, a second blood component region, and an interface region between the first and second blood component regions comprising at least three spaced apart sensing units that each senses the attenuation of energy emitted into the blood and generates a signal relating to the attenuation, at least one of the sensing units being located above the interface region and at least one of the sensing units being located below the interface region, and a processing element coupled to the sensing units including means for converting the signals to a signal vector of signal values having a shape approximated by a function, means for normalizing the signal vector, means for creating a vector of convolution signal values by multiplying the normalized signal vector by the function, and means for identifying the sensing unit associated with the highest convolution signal value to thereby identify the sensing unit closest to the interface region.

8. A system according to claim 7 and wherein the processing element includes an output for outputting the identity of the sensing unit associated with the highest convolution signal value.

9. A system according to claim 7 wherein the function is a sigmoidal function.

10. A system according to claim 7 wherein the normalized signal vector has a symmetric shape.

11. A system according to claim 7 wherein the normalized signal vector is normalized between −1 and 1.

12. A system according to claim 1 and wherein the processing element includes means for limiting the signal values of the signal vector according to prescribed criteria.

13. A blood component collection system comprising a chamber holding blood comprising a first blood component region, a second blood component region, and an interface region between the first and second blood component regions, an outlet path communicating with the chamber to convey at least one of the first blood and second blood component regions from the chamber, at least three spaced apart sensing units arranged along the chamber, each of the sensing units sensing the attenuation of energy emitted into the blood within the chamber and generating a signal relating to the attenuation, at least one of the sensing units being located above the interface region and at least one of the sensing units being located below the interface region, and a processing element coupled to the sensing units that locates the sensing unit closest to the interface region, while the outlet path conveys the at least one blood component region from the chamber, by following the steps of converting the signals to a signal vector of signal values having a shape approximated by a function, normalizing the signal vector, creating a vector of convolution signal values by multiplying the normalized signal vector by the function, and identifying the sensing unit associated with the highest convolution signal value.

14. A system according to claim 13 wherein the processing element includes an output controlling conveyance through the outlet path based, at least in part, upon identifying the sensing unit associated with the highest convolution signal value.

15. A system according to claim 13 and wherein the processing element performs the step of limiting the signal values of the signal vector according to prescribed criteria.

16. A system according to claim 13 wherein the function is a sigmoidal function.

17. A system according to claim 13 wherein the normalized signal vector has a symmetric shape.

18. A system according to claim 13 wherein the normalized signal vector is normalized between −1 and 1.

19. A method for monitoring a volume of blood comprising a first blood component region, a second blood component region, and an interface region between the first and second blood component regions comprising the steps of locating at least three spaced apart sensing units with respect to the blood volume, with at least one of the sensing units located above the interface region and at least one of the sensing units located below the interface region, sensing with each sensing unit the attenuation of energy emitted into the blood, generating a signal relating to the attenuation sensed by each sensing unit, converting the signals to a signal vector of signal values having a shape approximated by a function, normalizing the signal vector, creating a vector of convolution signal values by multiplying the normalized signal vector by the function, and identifying the sensing unit associated with the highest convolution signal value to thereby identify the sensing unit closest to the interface region.

20. A method according to claim 19 and further including the step of limiting the signal values of the signal vector according to prescribed criteria.

21. A method according to claim 19 and further including the step of outputting the identity of the sensing unit associated with the highest convolution signal value.

22. A method according to claim 19 wherein the function is a sigmoidal function.

23. A method according to claim 19 wherein the normalized signal vector has a symmetric shape.

24. A method according to claim 19 wherein the normalized signal vector is normalized between −1 and 1.

* * * * *